United States Patent [19]

Hardt

[11] Patent Number: 4,928,704
[45] Date of Patent: May 29, 1990

[54] EEG BIOFEEDBACK METHOD AND SYSTEM FOR TRAINING VOLUNTARY CONTROL OF HUMAN EEG ACTIVITY

[75] Inventor: James V. Hardt, San Francisco, Calif.

[73] Assignee: MindCenter Corporation, Palo Alto, Calif.

[21] Appl. No.: 304,979

[22] Filed: Jan. 31, 1989

[51] Int. Cl.$^5$ .............................................. A61B 5/04
[52] U.S. Cl. ................................ 128/732; 364/413.05
[58] Field of Search ..................... 128/732; 364/413.05

[56] References Cited

U.S. PATENT DOCUMENTS

| | | |
|---|---|---|
| 3,032,029 | 5/1962 | Cunningham . |
| 3,123,768 | 3/1964 | Burch et al. . |
| 3,524,442 | 8/1970 | Horth . |
| 3,533,003 | 10/1970 | Plaszczynski et al. . |
| 3,628,538 | 12/1971 | Vincent et al. . |
| 3,641,993 | 2/1972 | Gaarder et al. . |
| 3,753,433 | 8/1973 | Bakerich et al. . |
| 3,821,949 | 7/1974 | Hartzel et al. . |
| 3,896,790 | 7/1975 | Dikmen . |
| 3,905,355 | 9/1975 | Brudny . |
| 3,942,516 | 3/1976 | Glynn et al. ........................ 128/732 |
| 3,978,847 | 9/1976 | Fehmi et al. . |
| 3,983,865 | 10/1976 | Shepard . |
| 4,031,883 | 6/1977 | Fehmi et al. ........................ 128/732 |
| 4,136,684 | 1/1979 | Scattergood et al. . |
| 4,228,807 | 10/1980 | Yagi et al. . |
| 4,334,545 | 6/1982 | Shiga ................................. 128/732 |
| 4,461,301 | 7/1984 | Ochs . |

OTHER PUBLICATIONS

Plotkin, W. B., "On the Self-Regulation of the Occipital Alpha Rhythm: Control Strategies, States of Consciousness, and the Role of Physiological Feedback", *Journal of Experimental Psychology: General*, 1976, 105, 66–99.

Cleeland, C. S., Booker, H. E., & Hosokawa, K., "Alpha Enhancement: Due to Feedback or the Nature of the Task?", Psychophysiology, 1971, 8, 262–263.

Hord, D. & Barber, J., "Alpha Control: Effectiveness of Two Kinds of Feedback", *Psychonomic Science*, 1971, 25, 151–154.

Peper, E. & Mulholland, T. B., "Methodological and Theoretical Problems in the Voluntary Control of Electro Encephalographic Occipital Alpha by the Subject", *Biofeedback and Self-Control*, 1970, Chicago: Aldine-Atherton, 1971.

Paskewitz, D. A., & Orne, M. T., "The Effect of Cognitive Tasks on the Feedback Control of Alpha Activity", *Psychophysiology*, 1971, 8, 263.

(List continued on next page.)

Primary Examiner—Francis Jaworski
Attorney, Agent, or Firm—Townsend and Townsend

[57] ABSTRACT

A biofeedback method and system for use to train a person to develop useful degrees of voluntary control of personal electroencephalogram (EEG) activity. A plurality of EEG potentials from a plurality of locations on the head are individually amplified and filtered in accordance with strict criteria intended for processing in accordance within time constraints limited by natural neurological reactivity. Each resultant signal is processed to provide objective data on brain energies as a function of frequency. Data are presented in real time to the trainee in the form of preselected auditory tones and/or vibro-tactile stimuli indicating with high fidelity the details of EEG activity at a multiplicity of cortical sites. Features of auditory feedback promote learning as well as identification and elimination of spurious artifact states. At periodic intervals, the auditory feedback is supplemented by sensory presentation of digital scores summarizing performances in a metric proportional to brain energy output in the feedback parameters. The scores may be presented as illuminated numerical displays, aurally or both. The system is preferably in an environment designed to control the arousal level of the trainee and the degree of distractibility so as to maximize the learning of voluntary self-control.

37 Claims, 4 Drawing Sheets

OTHER PUBLICATIONS

Paskewitz, D. A. & Orne, M. T., "Visual Effects on Alpha Feedback Training", *Science*, 1973, 1981, 360–363.

Honorton, C., Davidson, R., & Bindler, P., "Shifts in Subjective State Associated with Feedback Augmented EEG Alpha", *Psychophysiology*, 1972, 9, 269–270.

Mulholland, T. B., "Can You Really Turn on with Alpha?", *The R. M. Bucke Memorial Society Newsletter Review*, 1972, 5(1&2), 32–40.

Walsh, D. H., "Effects of Instructional Set, Reinforcement and Individual Differences in EEG Alpha Training", *Proceedings of the Biofeedback Research Society*, Boston, Nov., 1972.

Walsh, D. H., "Interactive Effects of Alpha Feedback and Instructional Set on Subjective State", *Psychophysiology*, 1974, 11, 428–435.

Podlesney, J. A., & Raskin, D. C., "Biofeedback: A Failure to Enhance Alpha EEG", *Proceedings of the Society for Psychophysiological Research*, Galveston, Oct. 1973.

Williams, A. C., *Journal of Experimental Psychology*, 1940, 26, 413.

Kennard, M. A. & Willnor, M. D., *Diseases of the Nervous System*, 1945, 6, 337.

Stennett, R. G., *Electroencephalography and Clinical Neurophysiology*, 1957, 9, 131.

Costa, L. D., Cox, M., Katman, R., *Journal of Consulting Psychology*, 1965, 29, 90.

Kristin Shannon, "The New Biology of Genius: Brian Training for the Information Age", *Technological Forecasting and Social Change* 33, 299–310 (1988).

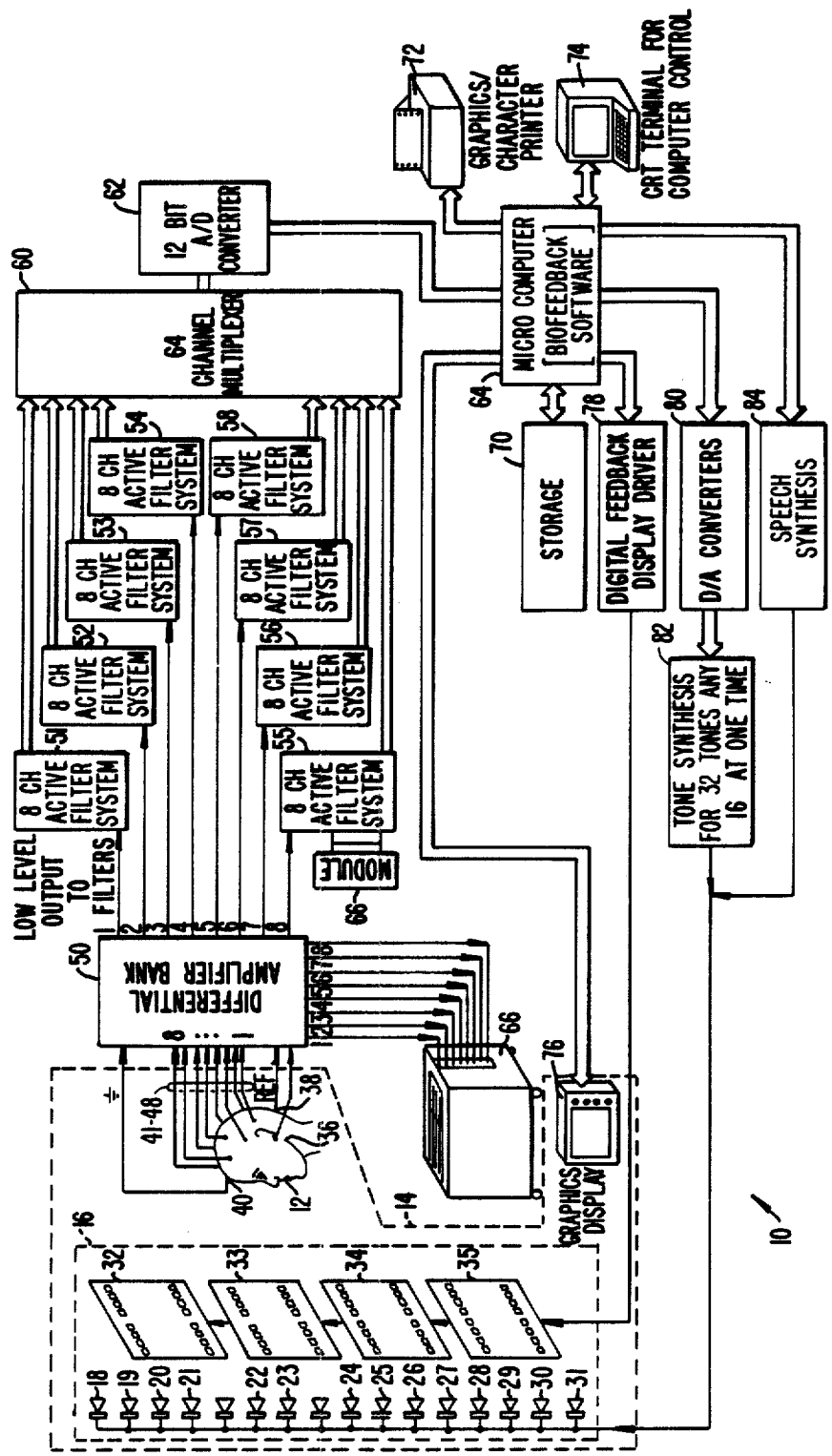
FIG._1.

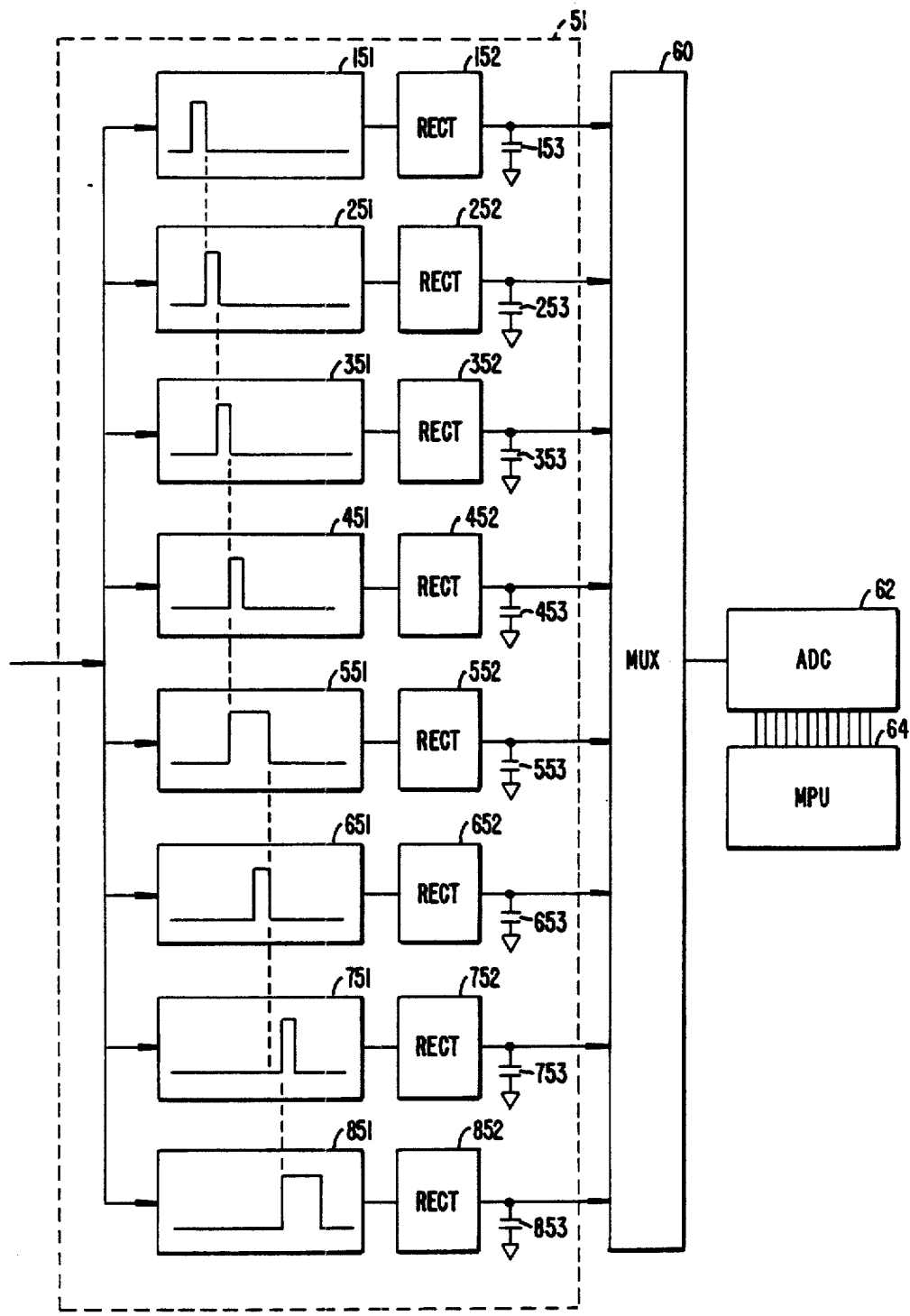
FIG._2.

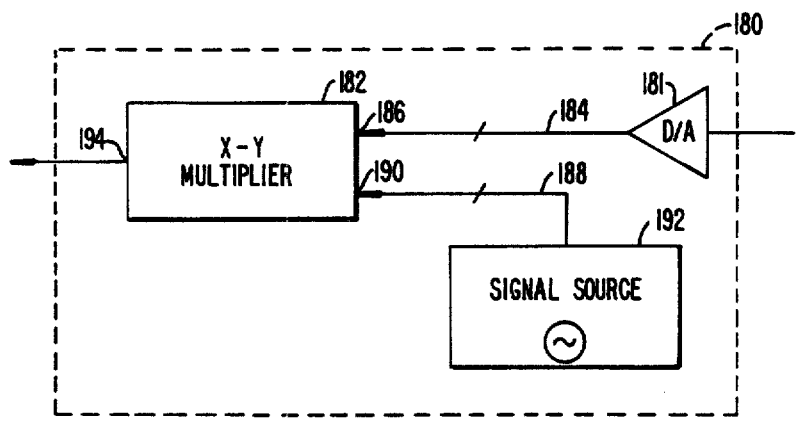
FIG._3.

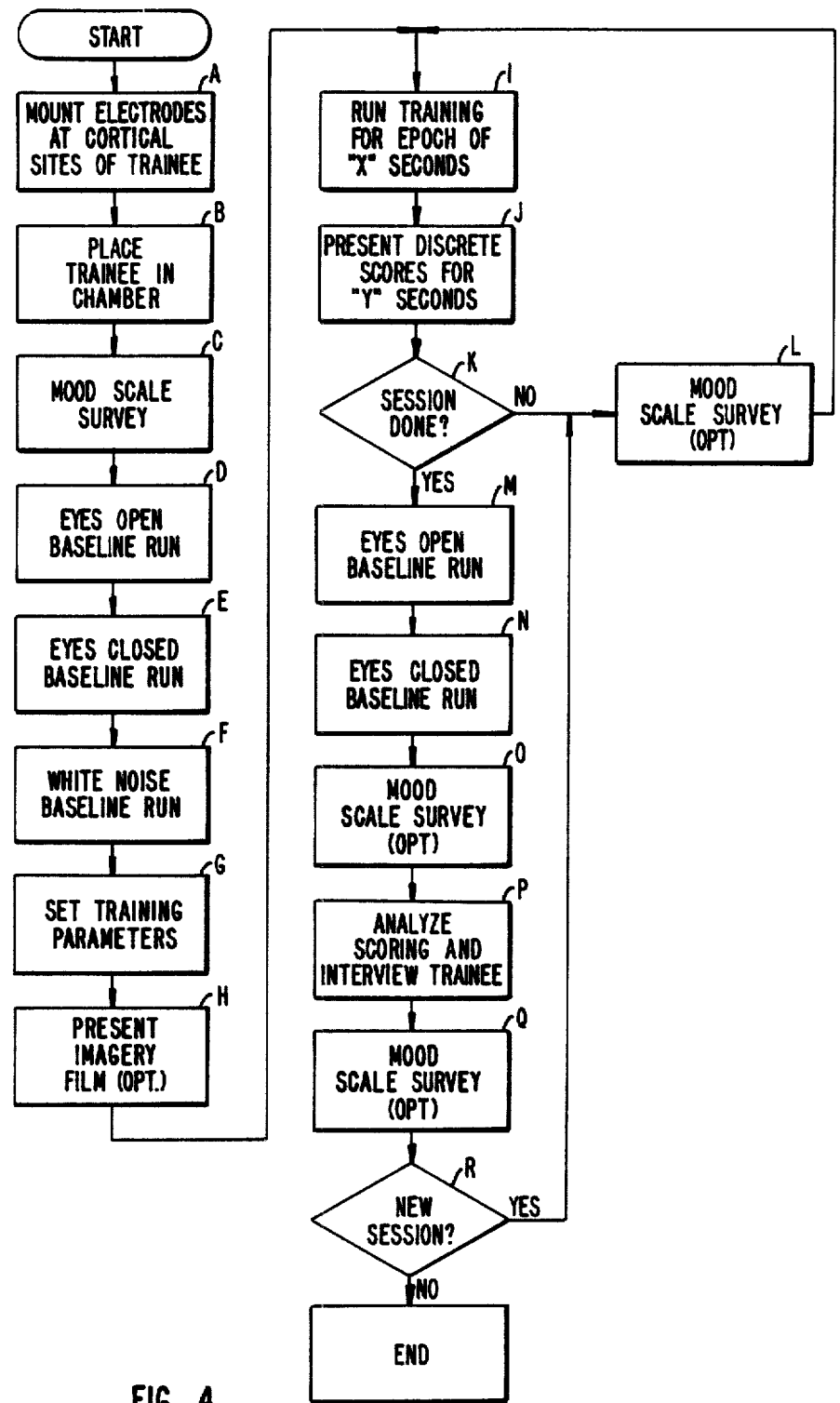
FIG._4.

EEG BIOFEEDBACK METHOD AND SYSTEM FOR TRAINING VOLUNTARY CONTROL OF HUMAN EEG ACTIVITY

BACKGROUND OF THE INVENTION

This invention was conducted in cooperation with the University of California San Francisco Medical School under partial sponsorship of the BioCybernaut Institute.

1. Field of the Invention

The invention relates to EEG biofeedback apparatus and to use of biofeedback information to foster rapid learning of EEG self-control. In addition, the invention relates to an EEG biofeedback apparatus for providing simultaneous, minimal phase delay feedback on multiple sub-bands of EEG filtered out of multiple independent EEG channels, each such channel derived from a different cortical location. Specific multiple subbands of EEG (delta, theta, alpha, beta, and subranges within each) can be combined in linear combinations to facilitate learning of complex, useful EEG patterns, and the sub-bands and subranges can be altered and redefined to permit adaptation of the system to unique individual requirements, designed to facilitate the learning of self-control of EEG activity.

The manifest purpose of biofeedback in general, and EEG biofeedback in particular, is to permit an individual to use the feedback information to learn a useful degree of voluntary self-control of a specific biofeedback parameter.

It is theorized that each of the major subbands of the EEG (delta, theta, alpha, beta) has unique bio-electric characteristics which correspond with unique subjective characteristics within the experience of the individual. Delta is observed most clearly in coma and deep sleep, theta in light sleep and drowsiness, alpha in a variety of wakeful states involving creativity, calming of the mind, and inner focus of awareness, and beta in alert wakeful situations with external focus.

Most of the focus of the prior art in EEG biofeedback has been directed to teaching voluntary control of EEG alpha activity only. Thus a major focus of this application will be on how this apparatus facilitates learning of EEG alpha activity. Alpha activity increases in creative people during periods of creativity and problem solving. Alpha activity increases in meditation. It is related to ability to withstand pain, and it is related to level of spiritual development in Zen meditation. Reduced alpha activity is associated with stress and anxiety. Thus, there are clearly important reasons for teaching people how to increase their EEG alpha activity with suitable EEG biofeedback apparatus and procedures.

2. Description of Prior Art

The following patents have come to the attention of the inventor as a result of a search:

| Patent Number | Issued | Name |
|---|---|---|
| 3,821,949 | July, 1974 | Hartzel et al. |
| 4,136,684 | January, 1979 | Scattergood, et al. |
| 4,228,807 | October, 1980 | Yagi, et al |
| 4,461,301 | July, 1984 | Ochs |
| Other patents referenced in the above patents are as follows: | | |
| 3,032,029 | May, 1962 | Cunningham |
| 3,123,768 | March, 1964 | Burch |
| 3,524,442 | August, 1970 | Horth |
| 3,533,003 | October, 1970 | Plaszczynski, et al. |
| 3,628,538 | December, 1971 | Vincent, et al. |
| 3,641,993 | February, 1972 | Gaarder, et al. |
| 3,753,433 | August, 1973 | Bakerich, et al. |
| 3,896,790 | July, 1975 | Dikmen |
| 3,905,355 | September, 1975 | Brudny |
| 3,978,847 | September, 1976 | Fehmi, et al. |
| 3,983,865 | October, 1976 | Shepard |

The following publications have come to the attention of the inventor:

Plotkin, W. B., "On the Self-regulation of the Occipital Alpha Rhythm: Control Strategies, States of Consciousness, and the Role of Physiological Feedback," *Journal of Experimental Psychology: General*, 1976, 105, 66–99.

Cleeland, C. S., Booker, H. E., & Hosokawa, K., "Alpha Enhancement: Due to feedback or the Nature of the Task?," *Psychophysiology*, 1971, 8, 262–263.

Hord, D. & Barber, J., "Alpha Control: Effectiveness of Two Kinds of Feedback," *Psychonomic Science*, 1971, 25, 151–154.

Peper, E. & Mulholland, T. B., "Methodological and Theoretical Problems in the Voluntary Control of Electro Encephalographic Occipital Alpha by the Subject," *Biofeedback and Self-Control* 1970. Chicago: Aldine-Atherton, 1971.

Paskewitz, D. A., & Orne, M. T., "The Effect of Cognitive Tasks on the Feedback Control of Alpha Activity," *Psychophysiology*, 1971, 8, 263.

Paskewitz, D. A. & Orne, M. T., "Visual Effects on Alpha Feedback Training," *Science*, 1973, 1981, 360–363.

Honorton, C. Davidson, R., & Bindler, P., "Shifts in Subjective State Associated with Feedback Augmented EEG Alpha," *Psychophysiology*, 1972, 9, 269–270.

Mulholland, T. B., "Can You Really Turn on with Alpha?" *The R.M. Buicke Memorial Society Newsletter Review*, 1972, 5(1&2), 32–40.

Walsh, D. H., "Effects of Instructional Set, Reinforcement and Individual Differences in EEG Alpha Training," *Proceedings of the Biofeedback Research Society*, Boston, November, 1972.

Walsh, D. H., "Interactive Effects of Alpha Feedback and Instructional Set on Subjective State," *Psychophysiology*, 1974, 11, 428–435.

Podlesney, J. A., & Raskin, D. C., "Biofeedback: A Failure to Enhance Alpha EEG," *Proceedings of the Society for Psychophysiological Research*, Galveston, October, 1973.

Berger, H., *Archiv fuer Psychiatry Nervenkrankheit*, 1929, 87, 527.

Berger, H., *Journal of Psychology and Neurology*, 1920, 40, 160.

Williams, A. C., *Journal of Experimental Psychology*, 1940, 26, 413.

Kennard, M. A. & Willnor, M. D., *Diseases of the Nervous System*, 1945, 6, 337.

Stennett, R. G., *Electroencephalography and Clinical Neurophysiology*, 1957, 9, 131.

Costa, L. D., Cox, M., Katman, R., *Journal of Consulting Psychology*, 1965, 29, 90.

The above references may represent relevant prior publications. These references describe many systems which measure human EEG activity, some of which are designed to provide feedback information to the person from whom the EEG signals are derived. While examples of the prior art suggest mechanisms for deleting and processing EEG activity, it invariably appears to be assumed that mere feedback, without regard to type or phase relationship, will permit learning of voluntary EEG control.

Prior art systems are limited in many ways. The channel capacity is limited. None of the known systems is designed with natural reactivity of the EEG in mind. And non of the known systems incorporates EEG detection and feedback mechanisms directed to learning control.

Some examples of the prior art actually incorporate as design objectives characteristics which have been found to be inimical to learning control of EEG (as for example U.S. Pat. No. 3,821,949, to Hartzel et al. and U.S. Pat. No. 4,461,301, to Ochs). Other prior art confound EEG beta activity and muscle activity and employ the resultant confusion in conjunction with imprecise EEG filtering to claim unique techniques of recognizing alpha waves and muscle potentials (for example U.S. Pat. No. 4,228,807). Simply recognizing the alpha waves and the muscle artifacts is not sufficient to promote learning. This fact is attested to by the large volume of published research papers wherein scientists using the best known examples of the EEG biofeedback art taught that is was not possible to teach their trainees any significant degree of voluntary control of EEG alpha activity (Cleeland, Booker, & Hosokawa, 1971; Hord & Barber, 1971; Peper & Mulholland, 1971; Pastewitz & Orne, 1971, 1973; Honorton, Davidson, & Bindler, 1972; Mulholland, 1972; Walsh, 1972, 1974; Podlesnoy & Raskin, 1973; Plotkin, 1976). Recent pronouncements by leading researchers in the field suggest a consensus opinion that people cannot learn voluntary control of their EEG alpha activity, and that work with other EEG parameters must await better equipment. Of particular note in the prior art are specifications as to degree of accuracy and precision required in an active feedback system. U.S. Pat. No. 3,821,949 to Hartzel et al. for example makes representations as to needed accuracy and precision. These representations have been discovered to be inadequate and apparently erroneous.

Against this background, the current invention constitutes a major advance over prior art.

SUMMARY OF THE INVENTION

According to the invention, an EEG biofeedback system is provided which comprises an environment free of unintentional aural and visual distractions wherein a pair of reference electrodes, a suitable ground electrode and a plurality of active cortical site electrodes used in monopolar configuration are placed on the head of a trainee with output signals directed to an equal number of EEG amplifiers. The output of each of the active cortical site electrodes is filtered into subbands or subranges of the EEG. The filtered signals are converted into aural or tactile response indicia and supplied in real time to the trainee in an environment with controlled spurious distractions to allow the trainee to respond instantaneously to biofeedback signals. In addition, cumulative or average rating values (numerical scores) are presented periodically to the trainee visually or audibly during breaks in a training session to permit the trainee to be informed of progress in biofeedback control.

In a specific embodiment, eight frequency subbands may be established: delta, slow theta, fast theta, slow alpha, middle alpha, fast alpha, slow beta, and fast beta. Frequency-domain filtering is accurately effected with minimal delay and precision greater than heretofore known or suggested. The present invention is based on considerations dictated by the natural reactivity of the EEG.

An important aspect of the present invention is the provision of EEG biofeedback indicia which: (a) permit easy recognition of specific subbands and subranges of the EEG; (b) permit easy recognition of peak performance within the chosen subbands and/or subranges; (c) permit recognition of the presence or absence of artifact conditions; (d) facilitate association of these recognitions with an often transient mental or subjective state accompanying them; and (e) facilitate the attainment of stable mental or subjective states which are associated with underlying EEG activity, which EEG activity is the subject of the biofeedback training.

As is hereinafter explained, learning control of EEG activity through EEG biofeedback is actually achieved by the learning of control over one's mental and emotional subjective states, and the whole of the technique involving apparatus, procedures, and environment must foster this latter function for optimal learning of EEG control to occur. The goal of such control is not control of measurable parameters, but the control of the mental and emotional subjective states associated with the objectively measurable EEG subbands and subranges.

A feature of the present invention is the presentation of both continuously-variable instantaneous, as well as intermittent discrete feedback information to the trainee. Continuously-variable instantaneous feedback preferably consists of tones chosen for frequency and waveform characteristics to facilitate the brain wave activity which is the subject of the EEG biofeedback training.

Another feature is the monotonic relationship between tone volume and instantaneous amplitude of the EEG parameter or parameters under feedback. Each different cortical site and/or each different EEG subband under feedback drives a tone of a different pitch originating from a separate speaker in a unique spatial location, up to a total of sixteen (16) speakers in one preferred embodiment. Thus, the trainee has both pitch cues and spatial cues to guide personal development of awareness and control of EEG and associated mental and/or emotional subjective states.

Another feature is that each of the tones has associated with it an alternate (secondary) tone which is automatically substituted for the primary tone whenever a specific amplitude threshold is exceeded. This has been found to be a preferred way to signal artifact without disturbing the feedback process. It also can be used to signal transient occurrences of peak performance in the biofeedback control task, thus reinforcing fleeting instances of peak performance as well as accelerating and motivating the feedback learning process. This feature also provides for "transfer of training" to situations outside the biofeedback setting by providing an adjustable level at which a "startle" or "orienting" response can be induced. To the extent a trainee can rapidly overcome startle response and reinstitute the mental and neural state currently under feedback, there will be more transfer of training from the feedback setting to the normal ambient environment of the trainee. The threshold of inducing the startle or orienting response can be adjusted so that beginning trainees can be spared undue distraction. Control can be strengthened later through the modulation of the adjustable startle. In this way learned self-control can be rendered stronger and more resilient and thus more useful.

Another feature is the provision of a minimum tone volume. Even in the absence of an EEG signal to activate the tones of the feedback system, tones are preferably never completely turned off. A sudden onset of tone would otherwise induce an undesired startle reaction. Any increase in target EEG activity from an initial zero level causes tone increase from a baseline level.

Another feature of the invention is a mechanism for presenting discrete scores at intervals summarizing performance according to the amplitude integral over the prior measurement period. The amplitude integral is preferable because it is proportional to the square root of brain energy and thus represents a physically real parameter. Presentation of this discrete scoring information, preferably in a visible digital readout form or in an aural value readout form, occurs at standard, but adjustable, time intervals at breaks in a training session. The information can be presented aurally through speech synthesis and/or through illuminated displays (e.g., LEDs or LCDs) which can be viewed by the trainee. Color of visual readout may be preselected to minimize distraction. Blue is preferred in this regard.

Another useful feature of the invention is the provision of output from the signal processing apparatus to a chart drive or the like so that a tracing of the EEG can be made for later inspection by the trainee and for ongoing inspection by the trainer/operator of the apparatus. A particularly useful diagnostic feature is the capability of producing a hard copy printout of the scores in a color graphics form for data analysis and for later viewing and review by the trainee.

Another feature is a graphics display monitor for presentation, in attractive color graphics, of a summary of the results of the entire training session and prior sessions for comparisons which both motivate and accelerate learning of EEG control.

These and other features of the invention will be explained upon reference to the following detailed description in connection with the accompanying drawings.

BRIEF DESCRIPTION OF THE DRAWINGS

FIG. 1 is a block diagram of a system according to the invention.

FIG. 2 is a block diagram of a representative active filter bank.

FIG. 3 is a simplified block diagram of a digital-to-analog converter according to the invention.

FIG. 4 is a flow chart of a method for training a trainee in accordance with the invention.

DESCRIPTION OF THE PREFERRED EMBODIMENTS

The invention of a biofeedback training method and system was guided by the following considerations: To maximize learning, feedback signals must be pleasant and attractive, the trainee must be motivated and sufficiently alert, and the presentation of the feedback signals must not in and of themselves reduce or block the EEG activity being trained. In addition, the feedback must be accurate and immediate, and the environment of the training session must be conducive to the task.

Referring to FIG. 1, there is shown in block diagram form a biofeedback training system 10 in accordance with the invention. A trainee 12 is situated in a training chamber 14 having directly controlled light and sound and at least indirectly controlled air and temperature. The temperature, air and humidity should be sufficiently moderate and comfortable so as not to detract. Temperature should be between 67° F. and 70° F., which is cooler than the range recommended by prior known biofeedback training guides. Clothing should be comfortable for the same reason. Light should be totally extinguishable from all sources, and there should be sufficient sound isolation to provide a still atmosphere. The training chamber 14 may therefore be a climate-controlled cubicle with adequate sound and light insulation, perhaps decorated in a calming or absorptive color such as deep blue or black and provided with a soundproof door.

Within the training chamber there may be provided one or more walls, herein a feedback wall 16, from or through which aural and visual feedback is presented. A plurality of loudspeakers 18–31 may be disposed at selected locations within the wall or at least behind a facade to provide audible feedback. In a full eight-channel system with eight active channels, as many as sixty-four speakers might be used. It is more practical, however, to provide only sixteen speakers for simultaneous controlled tone outputs through the speakers. It is intended that a tone of a different pitch originates from a separate speaker in a unique spatial location on the wall 16. Thus, the trainee has both pitch cues and spatial cues.

Visual displays 32–35 are disposed in the field of view of the trainee for example on the wall 16. The visual displays 32–35 are for providing intermittent discrete feedback information to the trainee to augment the continuous information provided through the speakers 18–31.

On the head of the trainee 12 are mounted as comfortably as possible a plurality of electrodes, including a pair of reference electrodes 36, 38 to the ear lobes, a suitable ground electrode 40 and a plurality of active cortical site electrodes 41–48 mounted in lateral pairs and used in monopolar configuration. The output signals directed to an equal number of EEG amplifiers in an EEG amplifier bank 50. The output of each of the active cortical site electrodes is amplified therein and filtered into subbands or subranges of the EEG in a corresponding number of multiple channel filter banks 51–58, and thereafter through a multiplexer 60 to a high-accuracy analog-to-digital converter, as explained hereinafter.

The amplifiers

Using high input impedance, low noise, low drift operational amplifiers, low current drain amplifiers are provided to permit optional use with battery power sources. Elimination of line voltage power enhances increases common mode rejection by eliminating all coupling to the 60 Hz AC line. A preamplifier section may be optionally built into a headband or lightweight headset which reduces the cable length from the head to the amplifier, thus reducing the unwanted pickup of 60 Hz and other radiated electromagnetic energy. This improves the signal to noise ratio and ensures that more accurate artifact-free EEG is presented to the filters. A multiple-channel chart recorder/polygraph 66 is coupled to appropriate outputs of the differential amplifier bank 50 to capture and record the raw EEG data prior to filtering.

Filters and Analog-to-Digital Converter

Analog bandpass filters 51-58 are provided in banks of eight. The bandpass filters 51-58 according to the invention may be active and are characterized by an elliptical response with 300–400 dB per octave rolloff at the skirts, 0.25 dB ripple in the passband and at least 50 dB rejection in the stop band. The filters 51-58 have a passband of only a few Hertz.

Referring to FIG. 2, there is shown an example of one filter set 51. The filter set 51 spectrally decompose the EEG signals through its input from an electrode into a plurality of subbands. The subbands may be chosen according to the training level of the trainee and object of the training. A number of specific subbands have been identified, as follows, and filters are configured to select the specific subbands: delta 151 [2.0–3.5 Hz], slow theta 251 [4.2–5.4 Hz], fast theta 351 [5.5–6.8 Hz], slow alpha 451 [7.5–8.8 Hz], broadband alpha 551 [7.7–12.6 Hz], fast alpha 651 [10.8–12.9 Hz], slow beta 751 [14.2–17.2 Hz], and broadband beta 851 [1 5.0–24.0 Hz]. Alternative subbands may be designated, such as broadband theta [4.0–6.7 Hz], middle alpha [8.9–10.7 Hz], and fast beta [17.3–24.0 Hz]. Under selected conditions, only a select few of the subbands are processed and made available as feedback signals. The outputs of the filter 51 may be made available as (a) filtered EEG, (b) filtered, full-wave rectified EEG, and/or (c) filtered, full-wave rectified and smoothed EEG. In the preferred embodiment, the filter signals are each directed at least through rectifiers 152, 252, 352, 452, 552, 652, 752 and 852 each having a smoother 153, 253, 353, 453, 553, 653, 753 and 853 across the outputs in the form of a capacitor to ground. The capacitors may have a value of 0.4 mfd for alpha activity to 1.2 mfd for beta activity corresponding to the appropriate subband. The outputs are fed into a multiple-channel multiplexer 60. The rectifiers and smoothers may comprise preferably 64 channels in a full function system, to obtain filtered, full-wave rectified, smoothed EEG output signals. The multiplexer 60 in turn directs the signals as analog samples to the 12-bit analog-to-digital converter 62 running at 35 kHz throughput. In this embodiment, a microcomputer 64 is provided for real-time processing of the output digital samples.

Referring again to FIG. 1, the microcomputer 64 samples the 64 filter outputs to obtain instantaneous EEG amplitude values which are used for computing the amplitude integrals and for driving the feedback, as hereinafter explained.

The filters 51-58 may be reconfigurable to provide feedback from and analysis of different EEG subbands. The analog filters 51-58 may for example each provide for a plug-in module 68 which sets the filter characteristics. The module 68 may be removable and replaceable to reconfigure the filters 51-58. In this way, the system 10 retains a degree of flexibility which renders it suitable for a variety of EEG feedback tasks.

The filters 51-58 must be highly linear, resistant to ringing and resemble the ideal box car bandpass filter. It has been found to be necessary to realize filter characteristics with great care because the purity of the filtered signal, uncontaminated by artifact, is essential to successful learning of the EEG biofeedback task. Each filter must be accurate beyond that which as been taught in the prior art. For example, U.S. Pat. No. 3,821,949 Hartzel et al. teaches that 10.0 dB rejection and 10% ripple is sufficient. It has been found that such a characteristic allows contamination of the filter output by adjacent EEG activity of up to 31.6% using real values of EEG signals. A filter whose output is nearly one-third contaminated by signals outside the stop band has been found to be unacceptably inaccurate and confusing to a trainee trying to learn EEG biofeedback with such a system.

In contrast, the preferred embodiment of the present invention provides accurate filtering to allow for accurate feedback. Only 2.8% ripple is allowed in the passband, rather than 10% the teaching of Hartzel et al.

The amount of contamination from the stopbands is much less also. In the 50 dB stopband configuration, the adjacent 100 microvolt theta and 100 microvolt EMG artifacts would each contribute only 0.3% contamination or 0.3 microvolt each, for a total contamination of 0.6 microvolt out of 10 microvolt of real signal. This is a 6% contamination situation rather than a 189% contamination in the Hartzel, et al. teaching. In a 100 dB stopband digital filter or switched capacitor filter configuration, the stopband artifacts would each contribute 0.001% or 0.001 microvolt each for a total contamination of 0.002 microvolt with 10 microvolt of real signal. This is only 0.02% contamination. The resulting greater accuracy of the EEG feedback signal promotes learning.

That there are numerous research reports on the failures to teach trainees voluntary control of their EEG highlights the importance of this distinction according to the invention.

Microcomputer

The microcomputer 64 serves a variety of control functions and has associated with it sufficient random access memory and mass storage 70 to carry out programmed functions. Also associated with the microcomputer are a color graphics and text printer 72, a control terminal 74 or equivalent and a graphics presentation display 76 which is in the chamber 14 as explained hereinafter. The peripherals provide conventional input and output functions in support of the control and analysis functions of the microcomputer 64, as well as additional sources of feedback to the trainee.

The microcomputer 64 is coupled to a variety of output devices to provide feedback into the chamber 14. There is provided, for example, a microprocessor-based digital display driver 78 which is coupled to drive digital devices such as the digital displays 32-35. There is also the graphics display 76. The driver 78 is preferably networked with the microcomputer 64 to relieve the microcomputer 64 of menial real-time processing tasks.

In addition there is provided a digital-to-analog converter bank 80 coupled to a tone synthesizer and output amplifier 82, which in a specific embodiment are also under microprocessor control. The digital-to-analog converter bank 80 comprises a plurality of digital-to-analog converter means 180, one per audio channel.

Referring to FIG. 3, in order to provide for a pleasing high-quality audio output, the digital-to-analog converter means 180 comprises an eight-bit digital-to-analog converter chip 181 coupled to an X input 186 of an X-Y multiplier 182, the multiplier 182 being coupled to receive at a Y input a variable analog biofeedback input signal 184 from an analog signal source 192. The preferred analog signal source 192 produces an analog sine wave signal output, and the multiplier 182 is functional to produce analog product at its output 194. One form of signal source is a synthesizer unit, such as a type 2206 synthesizer of EXAR Corporation of San Jose, Calif., configured to produce a synthesized analog digital sine wave. Other types of signal sources may be employed, such as the output of a synthesized musical instrument. The multiplier may be a type 1495 X-Y multiplier of Motorola, Inc. of Phoenix, Ariz. Other X-Y multipliers may also be employed.

Referring again to FIG. 1, the tone synthesizer 82 is provided with the features in accordance with the following considerations:

Feedback Tones

Tones are the principal mechanism for real-time feedback employed for EEG training in accordance with the invention. Tones must be maintained at substantial volume and duration for rapid learning of self control. Tone quality is also critical to learning control. It has been discovered in the course of work leading to the present invention that tone frequency is a critical determinant of learning. For example, tone onset causes blocking (abolition or diminution) of EEG alpha as a nonlinear function of tone frequency. It was discovered that blocking duration is minimal between about 400 Hz and 800 Hz and that above and below these frequencies, blocking duration rose rapidly. If tone onset occurs in response (feedback) to alpha onset and if tone onset causes alpha blocking, then the result is negative feedback and is thus unlikely to promote learning of alpha EEG control. According to the invention therefore, the tones are chosen to lie only between about 400 Hz and 800 Hz for alpha training.

In theta training, however, a principal problem is drowsiness with the trainee falling asleep, so a higher pitched more piercing tone is appropriate for theta training. This also allows nonoverlap between the alpha tones (about 400–800 Hz) and theta feedback tones (above about 800 Hz).

The waveform of the tone is also important to learning. It is easy to generate square waves and sawtooth waves electronically, but they have an unpleasant quality with abundant harmonics generated at the leading and trailing edges. Square waves are difficult to listen to at the high volume and for the long periods of time which are important for successful and rapid learning of EEG self control. Preferably one should use: (a) pure sine waves generated electronically and amplitude modulated by the envelope of the filtered, full wave rectified, smoothed EEG activity; or (b) pure notes of the trainees' favorite musical instruments. These may be digitally synthesized or digitally recorded and played back from digital information stored in ROMs rather than on disks. In both cases, the tones are available in a variety of pitches (frequencies) which are harmonious and aesthetic when all sounded together, and which are amplitude modulated by the envelope of the filtered, full wave rectified, smoothed EEG activity. The essential purpose here is to have the tones pleasing to listen to for long periods of time at loud and varying volumes, with a selection of tone frequencies designed to prevent or minimize negative feedback (reduction of EEG signal to tone onset).

The amplitude of the tone feedback should be linearly related to the amplitude of the instantaneous filtered EEG. The dynamic range of the system must be capable of reflecting the full range of EEG variations. However, this linear relationship does not mean that tone volume should go to zero when the feedback signal goes to zero amplitude. It is disruptive to learning to have the feedback tones shut off completely and then turned on, possibly suddenly. As a result there should be an audio offset, above zero, so that the tones are never completely off. Increases in feedback thus lead to mere increases in a tone volume which is already audible. This does not violate the linearity principle but does insure a continuity of sound even during lapses in the feedback signal. Continuity of sound facilitates learning and minimizes the disrupting effects of tone onset.

It is highly desirable to minimize the delay between the sensing of an EEG event and the presentation of that event to the trainee in the form of a tone. According to the invention, the feedback delay should be less than about 350 ms and preferably less than 200 ms to optimize feedback training. In the preferred embodiment the feedback delay is less than 100 ms, which is less than one alpha wave cycle.

The primary/secondary feedback tone feature is a desired mode of operation. The operator/trainer can, through the control console 74, set an adjustable amplitude threshold at which the primary feedback tone shifts (with no change in volume) to a secondary tone of a different pitch. This feature, plus its adjustable threshold of implementation allows for two very different and both important contributions to learning EEG self-control.

Primary/secondary feedback tone control is most important in early learning, when the trainee has not yet learned how to sit still and avoid movement which cause muscle electrical potential artifacts. The high quality of the filters 51–58 prevents contamination by most common EEG artifacts, but movements or muscle tensions can both originate electrical potentials which fall within the frequency range of the EEG, and thus would be passed by any EEG filter. Early in learning, in the first several days especially, such artifacts are common. In actual operation when such artifacts occur, they add to the existing filtered EEG activity, which they usually greatly exceed in amplitude. This causes the apparatus to shift each affected feedback channel from the primary to the secondary pitch, while preserving the current ambient amplitude accuracy of the signal. This sudden change of pitch becomes for the trainee the unmistakable signature of artifact, which he then swiftly learns to avoid, thereby establishing himself more readily in a comfortable long-term posture in which he can remain motionless and artifact-free and thus better able to learn the subtle task of EEG self-control.

A second factor of the primary/secondary tone shift is more important in later learning. In later learning the trainee masters how to avoid artifacts. The adjustable threshold of tone shift is thus most likely to be triggered by the emergence of sudden, high amplitude transients of the feedback signal. There may be probe signals the brain generates to test the new mode of being which is being trained for by the EEG feedback process. The probe signals are reflective of psychological and experiential transients important to the learning process. They are so important that merely to feed back the increased tone volume this increased EEG amplitude would probably be insufficient reinforcement for the breakthrough they presage. As a result, significant transients are highlighted according to the invention by the bold and highly perceptible signal of changing the pitch of the feedback tone. At such a point in the training process the pitches of the primary tones are familiar and well learned, so that the emergence of a different tone is a notable event. Together with proper instruction, the trainee should thereby be motivated to further develop the high amplitude ability presaged by the emergence of high amplitude transients within the frequency range of the feedback parameter.

As a further characteristic, the primary/secondary tone shift initially causes startle. The startle requires the advanced trainee to impose further self-discipline upon himself and his brain waves so as to be able to produce the EEG control and the underlying mental/emotional state at will and in a resilient manner not easily subject to disruption by external events.

It is desired that the audio tones be provided with control which ensures accurate and repeatable volume settings. Volume control should preferably interact with the volume settings at which the primary/secondary tone transition occurs. Specifically, when the digital volume control is increased to provide louder volumes for each successive day of training, such louder volumes should increase the likelihood that a transient in the EEG will trigger the primary/secondary tone shift. This feature also has the advantage of automatically providing increasingly vigorous guidance in avoiding movement and muscle artifact, because with increased digital tone volume settings ever more minute artifacts will trigger the secondary tones. Shaping of postural self regulation (which is an essential component of learning EEG self control) is provided automatically with the standard operating procedures of this apparatus working in concert with hardware and software features of the invention.

One serious problem with all biofeedback (EMG, temperature, EEG, etc.) is localization of control. In a preferred embodiment of this invention, there are provided a plurality of critical sites on the head of the trainee for electrodes for a plurality of EEG channels, each of which can give rise to a plurality of distinct feedback signals. The feedback tones (except for the primary and secondary tones of each channel) preferably originate from spatially separate speakers 18–31. The plurality of speakers with different pitches allow the trainee to usefully employ a plurality of feedback channels. With only one feedback site, the trainee learns to produce the changes desired in an area which narrows about the feedback site as training time increases. The standard means of preventing this is to continually change the feedback site. But this is impractical with EEG because EEG control at different critical sites requires often quite different strategies, and the existence of different strategies for subsequent sessions using different critical sites confounds learning. As a result, simultaneous feedback from multiple sites is preferred. This allows the trainee to choose his strategies and to discover which sites they affect. This actually speeds up learning because with a number of different sites, each responding to different strategies, the probability that whatever the trainee tries will lead to success at some site is increased every time the number of sites increases. The system according to the invention is always operated with a minimum of four different feedback sites, even for beginners. Too many sites at the beginning of training can be an overload of information, so beginners start with four feedback sites.

In addition, or alternatively, vibro-tactile feedback can be employed to provide feedback to the trainee. To this end, the voice coil of a speaker 18, or a vibrating motor or the like electromechanical transducer is placed in contact with the trainee. Vibro-tactile feedback has been found to positively reinforce alpha activity.

There is typically a problem of overload of information for beginners. To address the problem, it is provided that the audio tone volume and the digital scores may be set up to be mathematical combinations of the other feedback and/or non-feedback channels. For example, if a trainee wanted one tone/score system to be the sum or average of all the alpha channels on the left side of his head and another tone/score system to be the sum or average of all the alpha channels on the right side of his head, this could easily be accomplished merely by entering the proper codes into the CRT-terminal controlling the computer which runs the biofeedback system of this invention.

It is intended that there be presentation of digital scores providing summary information of the trainees' progress over brief epochs of time, such as two minutes. Human auditory memory integrates poorly over time so the trainees' judgment of success might be accurate on a moment-to-moment basis, but over a period such as two minutes trainees would judge their performance poorly based solely on audio tone volumes which fluctuate. One loud tone burst might be over-valued, leading the trainee to judge cumulative performance as better than it actually was. Accuracy is important, but not just accuracy of the apparatus. The apparatus must continually interact with the trainee to improve the trainee's performance and the trainee's accuracy of judgment of his own performance. Within this guideline, digital, cumulative scores are an important feature. In one preferred embodiment, four-digit scores are used. A score of 1500 may reflect 50 microvolt EEG activity. This dynamic limit allows use of the full dynamic range of a 12 bit A/D converter and makes the attainment of a 100 point increase a notable and experientially rewarding event. Also, it makes the attainment of a score of 1000 an especially rewarding event particularly since many people, if they train long enough can attain the 34 microvolt level needed to exceed a score of 1000.

The choice of scores and their microvolt equivalents may be an option of the user. Any consistent selection may be used which is suitable to the user's purpose so as to facilitate learning. An example may be instructive. The trainee may try one strategy for two minutes (an optimized epoch) and then try a different strategy for the subsequent two minutes. If the trainee were guided only by memory of when the feedback tones sounded loudest, he would often make inaccurate judgments even if the feedback tones themselves were absolutely accurate. The trainee however is prompted, according to the invention, by being given integrate digital scores, for example visually. The scores may be at variance with subjective impressions of success. The scores then become useful in correcting subjective impressions, thereby allowing the trainee to choose more effective strategies which in turn accelerate learning of EEG control. Given the example of employing two different strategies during two different epochs, digital scores giving cumulative performance related to total brain energy through the filtered passband will correctly identify the strategy which had more elements of correctness in it. Thus, the trainee's subjective impressions and specific mental states are reinforced at frequent and regular intervals to aid the trainee in discovering and then in maintaining the appropriate, possibly subtle psycho-neural state which has both the desired subjective qualities and the desired associated brain wave activity. Presentations of these scores necessarily interrupt the tone feedback, and so the scores are preferably presented only in dim lights (LEDs or LCDs) and for only brief periods (less than 8 seconds).

Referring again to FIG. 1, the system 10 may be optionally provided with a speech synthesizer 84 coupled between the microcomputer 64 a speaker system in the chamber 14 whereby the scores may presented aurally through computer-generated speech synthesis. The disruption of presenting scores should be minimal and brief, but the information is essential to rapid learning and it must be frequent since most individuals have difficulty holding any mental strategy unbroken for two minutes. In addition, the chamber 14 may be provided with a color graphics output display 76 whereby the trainee may be presented with a graphical representation of his cumulative record of scores, showing for example amplitude and channel as a function of time.

Referring now to FIG. 4, a preferred embodiment of the method according to the invention is presented. The method implements a training regimen to promote individual self-control of brain functions via biofeedback through aural and visual senses. First, the electrode array is emplaced at the selected cortical sites of the trainee (Step A). There is provided a ground and two references, as well as carefully-sited active electrodes, typically placed in laterally-symmetric pairs in order to sense surface brain potentials representative of brainwave signals to be subjected to training. The trainee is then placed in the training chamber, a darkened soundproof room with a comfortable chair and the audio and video output devices used for feedback training, and the training apparatus and regimen are explained to the trainee as needed (Step B). The trainee is often given an opportunity to ask questions, but normally no hints are given at the outset on how to enhance biofeedback control. More effective long-term results appear to correlate with the process of self-discovery of control.

Baseline testing is then generally conducted. A mood scale survey is typically given at the outset, at the end and up to a total of about four times per training session at various optional times in order to collect data to correlate brain events and psychological events (Steps C, L, 0 and Q). An "eyes open" baseline is then run which is designed to reveal the trainee's minimal alpha levels and to allow the operator to check out and calibrate all instruments, including the chart recorder/polygraph 66, any volume controls and electrodes (Step D). The "eyes open" baseline run is generally in the presence of bright light and a steady background tone, and the task is to focus on a specific object in the field of view. An "eyes closed" baseline is then run to determine the nature of brainwave activity in the absence of conventional stimuli (Step E). This is conducted in darkness with a steady background tone. A "white noise" baseline is then run in preparation for the actual training sessions or epochs (Step F). The white noise run is used to condition the trainee to attend to an auditory signal while allowing the mind to relax without loss of recollection ability. White or quasi-white Gaussian noise is provided in the chamber in the absence of light and tones. The noise may be steady or modulated slowly, as for example at the rhythm of the waves on a seashore, and random beeps are be injected in the white noise aperiodically. The baseline data are captured on the polygraph 66 and in a cumulative scoring log of the microcomputer 64 for later comparison.

At that point, all training parameters are set or checked for the actual training runs (Step G). The parameters include minimum primary and secondary tone volume, startle threshold (secondary tone onset threshold), volume multiplier, epoch duration and break duration. Optionally the trainee may then be presented with a film or video presentation of imagery, musical sounds and guidance narration (Step H). The presentation is intended to enhance the attention and concentration of the trainee in preparation for an actual biofeedback session.

The actual training sequence consists of two segments or epochs. The training epoch is conducted for a period of about 120 seconds (Step I). A break of about eight seconds occurs after each training epoch (Step J). The standard training epoch consists of feedback of tones spatially, within preselected frequency bands and enhanced with secondary tones (startle tones). During the break, audio feedback is suppressed, and discrete scores are presented for each active sensor or selected combination of sensors summarizing immediate past performance according to the amplitude integral over the prior measurement period. The amplitude integral is preferable because it is proportional to the square root of brain energy and thus represents a physically real parameter. Presentation of this discrete scoring information, preferably in a visible digital readout form or in an aural value readout form, occurs at standard, but adjustable, time intervals and are presented for a relatively short duration of about eight seconds against a dark background so as to minimize disruption of the training session. Color of visual readout may be preselected to minimize distraction. (Blue is preferred because has been found to be the least distracting color.) The training session is then generally repeated several times. If the session is to be repeated (Step K), a mood scale survey may optionally be given to compare psychological and brainwave activity (Step L).

Several types of training objects may be pursued in a training session. One training object is brainwave suppression wherein the trainee attempts to control brainwave activity by conscious suppression. A further training object is brainwave enhancement whereby the trainee attempts to enhance brainwave activity in response to feedback. Secondary tones may be injected in the audible feedback of the training session to assist the trainee in controlling response to startle and like disruptions. Secondary tones are introduced in real time to the output speakers whenever the brainwave activity in the subject cortical region exceeds the secondary tone threshold.

At the conclusion of the brainwave training session, more baselines are run, namely, an eyes open baseline (Step M) and an eyes closed baseline (Step N). There may optionally be a mood scale survey at this point (Step 0) or later (Step Q). At the conclusion of the training session, the operator analyzes the data and interviews the trainee (Step P) to reinforce any brainwave control which has been demonstrated. Interviews are important because the trainee is required to verbalize his reaction strategies, which reinforces memory of the strategies for future training.

A training session may be fully repeated, a new training session may be commenced, or the sequence may be terminated (Step R).

The invention has now been explained with reference to specific embodiments. Other embodiments will be apparent to those of ordinary skill in the art. For example, the invention can be used in group feedback therapy. In such a setting, each trainee can be placed in a separate chamber and presented with the same training session, or a group of trainees can be placed in a common chamber and each provided with one or more personal feedback channels which others in the group do or do not share, but in addition everyone has access to a group feedback signal which is the sum or average of their individual efforts. The group capabilities of this invention also suit it particularly well to other group training settings, such as hospitals, clinics, schools, and industrial settings where a plurality of users, each of whom log onto and off of the system in his own time and yet receives accurate, personal feedback training in his own EEG control in a setting wherein the economies of scale can, for the first time, be applied to biofeedback work. One system can be employed to train many persons at the same or overlapping times, which can dramatically reduce the cost of such training, thereby also making learning of EEG biofeedback easier for greater numbers of people. It is therefore not intended that the invention be limited, except as indicated by the appended claims.

I claim:

1. A method for training a person to develop useful degrees of voluntary control of personal electroencephalographic (EEG) activity, said method comprising the steps of:
   (a) placing a plurality of EEG sensors at a plurality of cortical sites on a head of said person;
   (b) placing said person in an environment of controlled light and sound to control the arousal level and the distractibility of the person;
   (c) sensing electric potentials from said plurality of cortical sites to obtain a plurality of channel signals in a plurality of channels;
   (d) individually filtering said channel signals within predefined frequency subbands, each said predefined frequency subband having an abrupt cutoff at a low-frequency skirt, an abrupt cutoff at a high-frequency skirt and near instantaneous propagation for processing in accordance within time constraints limited by natural neurological reactivity to obtain a resultant signal for each said channel;
   (e) processing each said resultant signal to obtain objective data on brain energies as a function of channel; and
   (f) presenting said objective data substantially instantaneously as feedback to said person to indicate to said person personal EEG activity at a said plurality of cortical sites within said predefined frequency spectra in order to facilitate voluntary conscious and unconscious control over said personal EEG activity.

2. The method of claim 1 wherein said presenting step comprises providing said feedback as varying audible signals.

3. The method according to claim 2 further including the steps of:
   (g) recording said objective data;
   (h) generating a metric of said objective data to obtain metric data;
   (i) processing said metric data over a therapy interval to obtain interval cumulative data;
   (j) interrupting said presenting step after said time interval; and
   (k) presenting said interval cumulative data to said person for a brief time period as a score after said therapy interval in order to allow said person to observe an objective measure of said personal EEG activity.

4. The method according to claim 3 wherein said presenting step (k) further comprises presenting a cumulative record of said scores visually showing amplitude and channel as a function of time.

5. The method according to claim 4 wherein said presenting step (k) further comprises presenting said visual scores in darkness.

6. The method according to claim 4, further comprising applying steps (a) through (f) to a plurality of persons concurrently.

7. The method according to claim 6, further providing at least some instantaneous and interval cumulative data as shared common data among said persons.

8. The method according to claim 3 wherein said metric generating step (h) comprises measuring brain energy output and said processing step (i) comprises averaging said metric data.

9. The method of claim 8 further including the step of:
   (1) providing controlled spurious audible signals to said person during said therapy interval in order to allow said person to learn to recognize said personal EEG activity in the presence of interference artifacts.

10. The method according to claim 3 wherein said feedback is a combination of said objective data.

11. The method according to claim 3 wherein said metric data is a combination of said objective data.

12. The method according to claim 3 wherein said interval cumulative data is representative of the amplitude integral of the filtered EEG.

13. The method according to claim 2 wherein said presenting step (f) comprises presenting a primary tone of a first frequency continuously during brainwave activity below a first level, presenting a secondary tone of a second frequency during brainwave activity above said first level, and wherein there is a unique one-to-one direct relationship between instantaneous amplitude of brainwave activity in a selected one of said predefined subbands and amplitude of said primary tone.

14. The method according to claim 13 wherein said amplitude is linearly proportional to instantaneous peak amplitude of a rectified and smoothed EEG signal within said selected one of said predefined subbands.

15. The method according to claim 13 wherein said primary tone is between about 400 Hz and about 800 Hz as a representative signal for alpha training.

16. The method according to claim 13 wherein said primary tone is above about 800 Hz as an example of a tone for theta training.

17. The method of claim 1 wherein said presenting step comprises providing said feedback as varying vibro-tactile signals.

18. The method according to claim 1 wherein said minimal delay is less than 350 ms.

19. An apparatus for training a person to develop useful degrees of voluntary control of personal electroencephalographic (EEG) activity, said apparatus comprising:
   (a) a plurality of EEG sensors, said sensors being for placement at a plurality of cortical sites on a head of said person;
   (b) an environmental chamber of controlled light and sound enclosing said person to control the arousal level and the distractibility of the person;

(c) means coupled to said EEG sensors for measuring electric potentials sensed by said EEG sensors from said plurality of cortical sites to obtain a plurality of channel signals in a plurality of channels;

(d) a plurality of bandpass filters coupled to said measuring means, at least one bandpass filter means for each one of said channels, each said bandpass filter means having a passband characteristic of a predefined frequency spectra having an abrupt cutoff at a low-frequency skirt, an abrupt cutoff at a high-frequency skirt and near instantaneous propagation for processing in accordance within time constraints limited by natural neurological reactivity to obtain a resultant signal for each said channel;

(e) means coupled to said bandpass filter means for processing each said resultant signal to obtain objective data on brain energies as a function of channel; and (f) means coupled to said processing means for presenting said objective data substantially instantaneously as feedback to said person to indicate to said person personal EEG activity at a said plurality of cortical sites within said predefined frequency spectra in order to facilitate voluntary conscious and unconscious control over said personal EEG activity.

20. The apparatus of claim 19 wherein said presenting means comprises audio signal generators having as input said objective data and as output varying audible signals as said feedback.

21. The apparatus of claim 19 wherein said presenting means comprises vibro-tactile signal generators having as input said objective data and as output varying vibro-tactile signals as said feedback.

22. The apparatus according to claim 21 wherein said providing means is a visual and/or aural score presentation means providing a plurality of score values.

23. The apparatus of claim 22 further including:

(k) means included in said processing means for providing controlled spurious audible signals to said person during said therapy interval in order to allow said person to learn to recognize said personal EEG activity in the presence of interference artifacts.

24. The apparatus according to claim 21 further including means for combining said objective data for feedback.

25. The apparatus according to claim 19 wherein said one bandpass filter is an elliptical filter having a rolloff of at least 300 dB per octave, less than 0.25 dB ripple and greater than 50 dB rejection outside of a passband.

26. The apparatus according to claim 25 wherein said bandpass filter has a passband for delta brainwaves of 2.0 Hz to 3.5 Hz.

27. The apparatus according to claim 25 wherein said bandpass filter has a passband for slow theta brainwaves of 4.2 Hz to 5.4 Hz.

28. The apparatus according to claim 25 wherein said bandpass filter has a passband for broadband theta brainwaves of 4.0 Hz to 6.7 Hz.

29. The apparatus according to claim 25 wherein said bandpass filter has a passband for fast theta brainwaves of 5.5 Hz to 6.8 Hz.

30. The apparatus according to claim 25 wherein said bandpass filter has a passband for slow alpha brainwaves of 7.5 Hz to 8.8 Hz.

31. The apparatus according to claim 25 wherein said bandpass filter has a passband for broadband alpha brainwaves of 7.7 Hz to 12.6 Hz.

32. The apparatus according to claim 25 wherein said bandpass filter has a passband for fast alpha brainwaves of 10.8 Hz to 12.9 Hz.

33. The apparatus according to claim 25 wherein said bandpass filter has a passband for slow beta brainwaves of 14.2 Hz to 17.2 Hz.

34. The apparatus according to claim 25 wherein said bandpass filter has a passband for broadband alpha brainwaves of 15.0 Hz to 24.0 Hz.

35. The apparatus according to claim 19 wherein said presenting means further includes digital-to-analog converter means for converting digital representations of said feedback from said processing means to analog signals for amplifications, wherein said digital-to-analog converter means comprises a digital-to-analog converter unit coupled to and X-Y multiplier having as a first multiplier input an analog representation of said digital representation of said feedback and as a second multiplier input an analog signal source.

36. The apparatus according to claim 35 wherein said signal source is an analog sine wave generator.

37. The apparatus according to claim 19 further including:

(g) means coupled to said processing means for recording said objective data;

(h) means included in said processing means for generating a metric of said objective data to obtain metric data;

(i) means included in said processing means for processing said metric data over a therapy interval to obtain interval cumulative data; and (j) means included in said processing means to interrupt said presenting means after said time interval for providing said interval cumulative data to said person for a brief time period as a score after said therapy interval in order to allow said person to view an objective measure of said personal EEG activity.

* * * * *